United States Patent [19]

Sachetto et al.

[11] 4,267,314

[45] May 12, 1981

[54] PROCESS FOR THE PREPARATION OF LACTOSYLUREA, ITS PURIFICATION AND ITS CONVERSION TO THE CORRESPONDING N-HYDROXYMETHYLATED DERIVATIVE

[75] Inventors: Jean-Pierre Sachetto, St-Julien-en-Genevois; Alain Regnault, Par Ornex, both of France; Sergio Cuccolo, Geneva, Switzerland; Herve Tournier, Valleiry, France; Jean-Michel Armanet, Onex, Switzerland

[73] Assignee: Battelle Memorial Institute, Carouge, Switzerland

[21] Appl. No.: 11,133

[22] Filed: Feb. 12, 1979

[30] Foreign Application Priority Data

Feb. 14, 1978 [CH] Switzerland .................. 1585/78

[51] Int. Cl.$^3$ .............................................. C07H 5/00
[52] U.S. Cl. ........................................ 536/53; 536/18; 536/22; 426/568
[58] Field of Search .......................... 536/53, 22, 18

[56] References Cited

U.S. PATENT DOCUMENTS

| | | | |
|---|---|---|---|
| 2,612,497 | 9/1952 | Meijer | 536/53 |
| 3,654,200 | 4/1972 | Hsu | 536/53 |
| 4,066,750 | 1/1978 | Smith et al. | 536/53 |

*Primary Examiner*—Johnnie R. Brown
*Attorney, Agent, or Firm*—Philip M. Dunson

[57] ABSTRACT

A process for the preparation of lactosylurea and the N-methylol derivative thereof which are usable as feed supplements for ruminants.

According to this process, lactose and urea are heated to 70°–110° C. with a minimum of water and, if possible, this water is eliminated during the reaction. The crude reaction product can be purified by grinding with ice-water or ethanol and subsequent draining so as to eliminate by dissolution in such solvents the unreacted urea.

The corresponding N-methylol derivative is obtained by the reaction with formaldehyde.

9 Claims, No Drawings

PROCESS FOR THE PREPARATION OF LACTOSYLUREA, ITS PURIFICATION AND ITS CONVERSION TO THE CORRESPONDING N-HYDROXYMETHYLATED DERIVATIVE

The present invention concerns a process for the preparation of lactosylurea, its purification and its conversion to N-methylol-lactosylurea. These compounds are useful as fodder ingredients for animals.

It is known that ruminants are capable, at least partially, to assimilate the nitrogen of non-protein materials such as urea and ammonium salts. Thus, in order to save vegetable feed-stuffs, fodders containing free urea are often fed to cattle. The urea is enzymatically decomposed in the rumen of these animals which liberates ammonia, the latter compound being used by the microorganisms of the digestive tract of the animals, together with other products of the digestion, for the synthesis of the amino-acids necessary to the build-up of living tissues. However, free urea can sometimes cause the formation in the stomach of the animals of an excess of ammonia which may lead to poisoning hazards for the animals and to a significant loss of nitrogen by excretion.

It was however found that it was possible to remedy such drawbacks by using, in place of the free urea, some products of condensation thereof with glucides, for instance glucosylurea and xylosylurea, which products have definite advantages. Thus, in the case of fodder containing, for instance, glucosylurea, the enzymatic hydrolysis of this compound and the consecutive liberation of $NH_3$ are much slower and, independently of the suppression of the poisoning risks the assimilation of the feed-stuff and the take-up of the free ammonia are definitely improved. A short summary of the prior-art in this field can be found in Swiss patent application No. 7159/77 of the present applicant.

Thus, it has been proposed in the past to use several glycosylureas as feed supplements in fodders, for example the acid catalyzed condensation products between urea and molasses or the products of hydrolysis of wood and of cellulose. Recently, (Proc.Nat.Soc. 34 (1975), 90A; U.S. Pat. Nos. 3,677,767 (CARGILL)and 4,066,750 (ASTRA)) it has been proposed to use lactosylurea for this purpose, the preparation of which has been disclosed in the following references: Rec.Trav.-Chim. 22 (1903), 72-77 and Berichte 59B (1926), 69. According to one embodiment, the process of preparation consisted in heating for several days the lactose, either in crystalline form or precipitated from whey with rennet, with urea in aqueous solution in the presence of a mineral acid, e.g. $H_2SO_4$. According to this prior-art, the temperature should not exceed 60° C. for fear of decomposing the disaccharide into hexoses. Such a decomposition was mentioned in U.S. Pat. No. 2,612,497 (MEIJER) which indicated that, in order to form ureido-hexoses in such conditions (for instance between 60° and 100° C.) one could start with disaccharides such as lactose and maltose which would undergo hydrolysis into monosaccharides before condensing with urea.

According to another embodiment, one heats for 15 hrs at 70° C. a diluted aqueous solution of lactose (40-50% by weight) and urea with a relatively high proportion of a mineral acid (about 10% by weight) which provides conversion ratios of lactose to lactosylurea reaching 85%. However, this method was not suitable for directly isolating high purity lactosylurea because the acid solution had to be first neutralized, then it had to be concentrated to precipitate the impure lactosylurea which was subsequently recrystallized, for instance with water.

It has been surprisingly discovered now that by working with only small quantities of water and acid, it is still possible to obtain lactosylurea with an excellent yield at temperatures above 70° C. which permits considerably reducing the reaction time and is much more economical.

Thus, the process of the invention, in which one heats lactose and urea in the presence of water and an acidic catalyst, is characterized by the fact that one operates at a temperature of at least 70° C. and not in excess of 110° C. with a quantity of water that is kept to a minimum although sufficient to maintain the reaction mixture fluid enough to be agitated (at least at the beginning of the reaction) and stiff enough to be coated on a horizontal surface without collapsing. It may be further advantageous to operate in a manner such that said water progressively evaporates during the reaction period, this being particularly valid if it does not become necessary at the end of the reaction to eliminate from the lactosylurea obtained the residual unreacted urea and lactose as well as the acid catalyst.

By proceeding in this manner, one can easily attain yields of about 85% after only 2 hrs at 110° C., this figure being significantly improved by longer heating or by working under reduced pressure so as to accelerate the removal of the water produced by the reaction. It should be moreover remarked that the optimum working temperature depends on the kind of catalyst selected as will be seen hereinafter.

As the starting lactose, one can use crystallized lactose or crude lactose monohydrate which is obtained by concentration of deproteinized lactoserum, a very cheap product.

As acid catalyst, one can use in the present process the usual catalysts for condensing ureas with sugars, e.g. $H_2SO_4$, $H_3PO_4$, HCl, $H_2NSO_3H$, etc. . . . One prefers using $H_2SO_4$ in quantities of about 0.5-2% by weight of the reaction mixture. Also, it is preferable to add the acid catalyst gradually during the reaction period, in order to compensate for partial neutralization of the acid by the ammonia possibly liberated according to the following reaction:

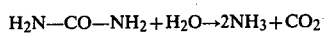

$$H_2N-CO-NH_2 + H_2O \rightarrow 2NH_3 + CO_2$$

Indeed, it has been noticed that at the highest temperatures of the previously discussed range, there exists some tendency of the salts formed between the acid used as catalyst and urea to decompose; this trend depends, moreover, on the nature of the acid which forms said salt. Thus, for instance, the sulfate of urea shows a tendency to decompose only above 90° C. whereas the phosphate of urea is less stable and starts decomposing around 75° C. The optimal reaction temperature will therefore be the temperature at which the most favorable compromise is achieved between the reaction rate which increases with temperature and the decomposition of the urea salts which require catalyst replenishment with fresh portion of the acid although the concentration of which must be desirably kept at minimum. When $H_2SO_4$ is used as the catalyst, the preferred temperature interval is 75°-85° C.

It should be further noted that the above discussion concerning the relative stabilities of urea salts at various temperatures is only valid, in absolute value, for a given concentration of the ingredients in the reaction mixture. If the water concentration is decreased, the deomposition trend at a certain temperature also decreases by virtue of the mass-action law. Consequently, if water rapidly evaporates during the condensation reaction the urea decomposition trend loses significance and the heating temperatures can be higher and, simultaneously, reaction periods can be shorter.

The amount of water to be added to the reaction mixture is as small as possible with the provise that the mass should be kept fluid enough to be agitated, at least during the first period of the reaction. For optimum yields, the amount of water should preferably not exceed 20-25% by weight of the reaction mixture.

It will be noted, in another connection, that the products resulting from the acid condensation between urea and saccharides already known in the art and used as feed-stuffs are mixtures, generally simply neutralized, containing high proportions of unreacted urea and sugars. Now, the present Applicant has found, as indicated in its previous Swiss application No. 7159/77 (U.S. application Ser. No. 913,834, filed June 8, 1978), that the glycosylureas when crystallized and purified from the free urea have great advantages over the above mentioned mixtures of condensed products for livestock feeding. Thus, for instance, synthetic glucosylurea, when freed from the unreacted urea it contains in the crude state, can not only liberate its ammonia at a very moderate rate, but it also very surprisingly favors the digestion and the assimilation of ordinary cellulosic products ingested simultaneously. The addition of purified glycosylureas to the cellulose rich cattle fodders therefore pursues a double objective: to retard the liberation of ammonia from urea and, thus, favor its assimilation by the animal and, simultaneously, improve the digestion of the cellulosic products present in such feed-stuffs.

In this connection, it was found that the lactosylurea prepared by the above disclosed process could be purified by eliminating the residual untransformed urea up to a level not exceeding 2.5%, this being achieved by treating the reaction mass with water or a hydrophilic solvent and by separating afterwards the purified insoluble product from the liquid that contains the impurities. Thus, according to a first embodiment, after cooling the crude reaction mass, the latter is ground and milled with ethanol after which the purified lactosylurea is separated from the ethanol by filtration. Ethanol indeed possesses the unexpected property of selectively dissolving the untransformed urea with the exception of a small amount thereof which remains combined with the acid catalyst as a urea salt. In general, this residual contamination by urea does not exceed 2.5%.

According to another embodiment, the crude reaction mass is taken and poured (preferably when it is still warm and fluid enough) into ice or ice-water, the temperature, after this treatment, being around 5°-30° C., then the undissolved solid is filtered or centrifuged, the impurities to be eliminated (i.e. the acid catalyst, the free urea, and part of the unreacted lactose) being removed with the mother-liquors. It should be remarked that, taking into account the practically complete removal of the unreacted urea by this purification method, it may be advantageous, in order to improve the yields of condensation between lactose and urea, to use at the start an excess of urea relative to the lactose. Naturally, in such case one can recover thereafter the urea in excess by the concentration and the crystallization of the washing mother-liquors according to usual means.

Lactosylurea can be added to the fodder of animals in crystalline form (by distributing in straw or hay) or in the form of an aqueous solution. It can also be mixed with meals or cereals (barley, corn, wheat). As such, it has very interesting properties regaring the slow release of combined nitrogen but this action can be improved if it is converted into the corresponding N-methylol derivative by the reaction with formaldehyde. This reaction can be carried out by usual means, i.e. by dissolving the lactosylurea in 30% aqueous formaldehyde then alkalinization with sodium hydroxide, heating a few hours and concentrating until crystallization occurs.

The following Examples illustrate the invention.

EXAMPLE 1

In a one liter cylindrical reactor with wide opening and equipped with a powerful stirrer, there were mixed 36 g of lactose monohydrate (0.1 mole) and 10 ml $H_2O$. The temperature was raised to 70° C. After 10 min under agitation were added 60 g (1 mole) of urea and there was obtained a mass viscous enough to be agitated without difficulty. After full homogenization of the mass, there were added under stirring and at 70° C., 324 g of lactose monohydrate (0.9 mole) by portions of 36 g (that is 9 fractions) at the rate of one portion every 10 min. After the addition of each fraction, there was added a minimum of water in order that the agitation could be pursued, the mixture still being in a pasty state. This addition did last about 90 min, the total addition of water was around 50 ml and should not exceed significantly this amount. The added portions of water were of a few ml each time. After having added all the lactose, there were added 3 ml (5.5 g) of $H_2SO_4$ 98% dissolved in 10 ml $H_2O$ and the mixture was kept under agitation as long as possible. After 8 hrs, 20 ml of water were still added because the mixture was becoming too stiff, and heating was continued. After 10 hrs, the agitator was stopped but the heating at 70° C. was continued. After 23 hrs, there was obtained a white mass sufficiently brittle to be easily broken and removed from the reactor. This mass weighed 450 g. The total free urea remaining in the mass, as determined from the reaction with urease, was 13.5 g (3% by weight) and its content in sulfuric acid was 5.5 g (1.22%). The yield of condensation relative to the urea was (60-13.5)/60=78%.

Since the mixture contained 5.5 g of pure $H_2SO_4$ (56 mmoles) and 13.5 of free urea (225 mmoles), it was assumed that ¼ of the non condensed urea was bound to the acid in the form of sulfate, the remainder being in non-salt form (it is assumed that one mole of sulfuric acid can bind one mole of urea).

Half of the product (225 g) was mixed with ethanol (500 ml) in a mixer for 3 min. The obtained suspension was filtered and the remaining 225 g of the product were taken again with the ethanol washing liquors from the first treatment. The combined washed products showed white and crystalline after filtration. After drying for eliminating the rest of the ethanol, there were obtained 378 g of a non-hygroscopic white crystalline poweder containing 0.56% of urea (2.11 g) and 0.33% of sulfuric acid (1.24 g), that is 35 mmoles of uncondensed urea and 12.6 mmoles of sulfuric acid (measured by alkali titration).

This indicates that the residual sulfuric acid must have been entirely combined with the urea in excess, in the form of urea sulfate. 85% of the non condensed urea ((225−35)/225) and 77.5% of the sulfuric acid ((5.5−1.24)/5.5) had thus been eliminated by washing.

The content of nitrogen in the product was 5.41% (as measured by elemental analysis), of which 0.25% corresponds to uncondensed urea and 5.16% to condensed urea. Thus the weight amount X/of lactosylurea in the mixture was given by [378−(2.11+1.24)]·5.16=X·7.29 (7.29 being the N weight % of lactosylurea). Thus, X=(374.65×5.16)/7.29=265.2 g (total weight of the lactosylurea), which means, calculated in % of the mixture: 265.2/378=70.1%. Therefore, the effective yield of the reaction was 265.2/384=69% (384=Mw of lactosylurea). Hence, the product mixture consisted of:

265.2 g of lactosylurea, 119.47 g of lactose monohydrate, 2.11 g of non condensed urea, partly as the sulfate, and 1.24 g of sulfuric acid as urea sulfate.

The crystalline product decomposes between 200° and 210° C. whereas pure lactosylurea has a M.P. of 230°−240° C. (dec.).

By evaporation of the washing alcohol, there could be recovered a solid residue consisting essentially of urea (11.39 g), part of which was in the form of urea sulfate linked to 4.26 g of sulfuric acid. This residue can be recylced in a further operation.

EXAMPLE 2

Same as Example 1, but replacing crystallized lactose monohydrate with crude lactose monohydrate obtained after concentration of deproteinized lactoserum. This crude lactose can be prepared as follows:

One liter of deproteinized lactoserum containing a concentration of lactose of 166 g/l and about 34 g/l of mineral salts and protein residues was concentrated as 70° C. under reduced pressure in a rotating evaporator until the volume was 280 ml. The concentrate was cooled and seeded with a few crystals of pure lactose which caused, after some time of standing, the crystallization of 150 g of relatively pure lactose. This quantity corresponds to a yield of about 90%. The mother-liquors furnished, after evaporation, a thick residue containing the rest of the lactose (about 16 g) and the mineral salts and the protein residues (30 g).

After the reaction of this purified lactose (360 g) with 60 g of urea as in Example 1, there were obtained 391 g of a solid homogeneous product with a hazelnut color containing 4.83% by weight of free urea (18.8 g, 0.31 mole). The yield of the condensation reaction was therefore 69% which is slightly inferior to the yield obtained with crystallized lactose.

The product was treated with ethanol as in Example 1 which permitted reducing the free urea content from 4.83% to 2.5% by weight. Simultaneously, the content in sulfate ions present in the mixture was decreased from 1.22% to 0.69%.

EXAMPLE 3

Same as Example 1 but replacing crystallized lactose monohydrate by impure lactose monohydrate obtained by evaporation to dryness of deproteinized lactoserum. The product thus obtained (mixture of lactose 83% and salts and protein residue) was sticky and hygroscopic. The reaction was performed according to the method of claim 1, by using 433 g of said mixture, i.e. 360 g of lactose. The product obtained appeared as a pasty mass containing 7.4% of free urea but, after treatment with ethanol as described in the previous Examples and drying under vacuum it turned out into a solid crystalline product. There were thus obtained 385 g of product containing 2.5% of unreacted urea and 0.67% of sulfate ions. Taking into account that the starting reaction mass contained 13.85% of free urea, the yield of the condensation is given by $$(13.85-7.4)/13.85=46.57\%$$

which is significantly lower than the yields obtained with the purer lactoses of Examples 1 and 2.

EXAMPLE 4

360 g (1 mole) of lactose monohydrate were mixed in a reactor with 60 g (1 mole) of urea and 100 ml of an aqueous solution containing 5.5 g of concentrated $H_2SO_4$. Heating was started and the temperature was raised gradually to 110° C. in 1¼ hrs. The amount of free urea was measured at this time and was 4.77%. The temperature was maintained at 110° C. for 2 hrs, after which the urea content was 2.34%. Heating to 110° C. was continued and the urea continued to decrease but very slowly: 2.31% after 4 hrs, 2.01% after 6 hrs, 1.97% after 8 hrs.

It was assumed that the reaction could be stopped after 2 hrs at 110°, because after such period 410 g of dry product containing about 9.4 g of free urea were recovered. Hence, the yield of the condensation (weight of combined urea/weight of initial urea) was: (60−9.4)/60=50.6/60=85%.

This yield was consequently higher than that obtained after heating 23 hrs to 70° C. (see Example 1). The mixture was treated with ethanol in a mixer, after which the hazelnut colored product was separated by filtration. After drying, there were obtained 370 g of product. This washed and dried product contained 1.68% of free urea. The nitrogen content was 6.35% which corresponded to a total urea content in the product (free+combined urea) of 14%.

If one computes the ratio between the amount of combined urea calculated by this methode and that of the total urea of the product, one obtains: (14−1.68)/14=12.32/14=0.9 i.e. the amount of combined urea is 90% of the total urea. This result corresponds approximately to the yield calculated above.

EXAMPLE 5

Continuous preparation of lactosylurea.

360 g of lactose monohydrate (1 mole) were mixed with 60 g of urea (1 mole) and 10.6 ml of a solution made up of 100 ml of $H_2O$ and 6 ml of 98% $H_2SO_4$. The mixture was melted and deposited as a thin layer on the moving belt of a tunnel oven. This oven was equipped with a system for controlling its temperature in a first third of its length (zone I) according to a temperature gradient and, in the second ⅔ of its length (zone II), at a constant temperature. Zone I was subjected to a temperature gradient ranging from ambient, at the entrance, to 100°−110° at the end of zone I; zone II was maintained at a constant temperature of 100°−110° C. The mixture coated on the belt thus penetrated into the tunnel and was gradually heated, in 1½ hrs, to 110° after which it entered zone II where it stayed for 2−3 hrs at 110° C. At the exit of the tunnel, the mixture was cooled and had the aspect of a slightly foamy, crystalline, light brown material, easy to remove from the belt with a doctor-knife and which could be ground into a powder. This product was collected in a continuous manner and about 400 g were obtained.

The total nitrogen content of this powder was 7.44% and the free residual urea content was 2.3% by weight, which indicates that about 85% of the initial urea had combined and that 15% thereof was in the form of free urea and urea sulfate. Although the amount of this residual urea, free or in salt form, is low enough not to be a harmful impurity when the product is used as a feed-product (there remains 0.15 mole of unreacted urea for 0.112 mole of sulfuric acid), it was possible to eliminate this impurity by treating the powder in a mixer in the presence of alcohol according to the directions given in Example 1. By this means, up to 80% of the residual urea can be eliminated.

EXAMPLE 6

Preparation of N-methylol-lactosylurea.

Crystallized lactosylurea (34.4 g; 0.1 mole) was dissolved in an aqueous solution of 50 ml of water and 15 ml of 40% aqueous formaldehyde (0.2 mole of HCHO). The mixture was made alkaline to pH 9 with 5% aqueous NaOH and then it was heated 5 hrs to 30°-40° C. Afterwards, it was concentrated under the water pump (10 Torr) without exceeding 40°-45° C. until the liquid became syrup-like. Then, slightly warmed ethanol was added until the solution developped a persistant cloud after which it was allowed to stand in the cold overnight. The crystalline solid which had formed (27 g) was collected and recrystallized twice in 70–80 % alcohol.

EXAMPLE 7

In a 250 reactor with glazed inside, there was dissolved urea (37 kg; 617 moles) in water at 40° C. (30 kg). Then, under stirring, there was added 98% pure lactose monohydrate (150 kg; 408.3 moles) and the whole was heated to 80° C. The mixture that formed was viscous but easily stirrable with the agitator. The pH of the mixture was then lowered to 1.9–2 by adding, at 80° C., about 8–10 kg of a diluted aqueous solution of $H_2SO_4$ (1 volume of acid for 5 volumes of water); then, progressively during the reaction, further portions of diluted $H_2SO_4$ were added in order to continuously maintain the pH around 1.2–2. Practically, this was achieved with a metering pump providing the diluted acid and placed under the assistance of a pH-meter controlling device which caused the pump to operate or stop depending on the pH variations with time. The acid addition rate during the reaction was about 1 liter/hr. The evolution of the reaction was followed by measuring the optical rotatory power of the mixture by means of a usual polarimeter, the specific rotation of pure lactose being $[\alpha]_D = 52.4°$ (starting conditions). Samples: 2–4 g dissolved in 40 ml $H_2O$; optical tube 200 mm. The lactosylurea rotation being only 1.1°, this was neglected in the above kinetic meansurements. After about 6 hrs at 80° C., there had been added about 17 kg of diluted acid (i.e. 4.5 kg of $H_2SO_4$, that is 1.92% by weight of acid relative to the total mixture, and a total of 18% of water), and the optical rotation measurements indicated a lactose conversion extent of 85%. The reaction was stopped and there were added to the mixture 40 kg of crushed ice. After dissolution of this ice under agitation, the colorless solid which formed was separated be centrifugation and washed with 20 l of ice-water. After draining, there were collected 140 kg (81%) of lactosylurea monohydrate having the following properties measured by analysis according to usual means: %N: calculated 6.96; found 6.73. Free residual urea <0.3%. Residual sulfuric acid <0.1% $[\alpha]_D^{20} + 1.1°$. F. 240°–245° C. (dec.), initial discoloration around 230° C.

It will be remarked that, in the above preparation embodiment, if the temperature is much above 80° C., the quantity of acid must be increased due to the tendency of the urea salt to form ammonia which acts as a neutralizer of the acidity. Further, the presence of too much water produces a decreased yield of the condensation because of the displacement, toward the left, of the equilibrium

lactose + urea ⇌ lactosylurea + water

It is therefore preferable to operate in the presence of a minimum of water and acid and by controlling the pH below 2. Moreover, the presence of an excess of urea (1.5 equivalent for 1 equivalent of lactose) favors the yield of the conversion of lactose to lactosylurea; however, it becomes then useful to recover the urea dissolved in the washing liquors and to recycle it.

The lactosylurea obtained without further purification according to the above process is, in contrast with the corresponding products of the prior-art, non-hygroscopic and can be easily used for the manufacture of excellent cattle fodders by mixing with other ingredients (meals, premixes, oil-seed cakes, flavors, etc . . .).

What we claim is:

1. A process for the preparation of lactosylurea suitable for supplementing nitrogen to reminants that comprises condensing lactose and urea in the presence of water and an acid catalyst at a temperature between 70 and 110° C. with a minimum quantity of water although sufficient to keep the reaction mixture fluid enough to be agitated but also stiff enough to be spread on a horizontal flat surface without collapsing.

2. The process of claim 1, wherein the water is progressively eliminated during the course of the reaction.

3. The process of claim 1, wherein after the reaction of condensation is terminated, the reaction mass is treated with water or a cold hydrophilic solvent, then the resulting crystallized solid is separated from the liquid so that the still unreacted products which remain dissolved in the liquid are removed from the solid, and thus a solid lactosylurea of very high degree of purity is obtained.

4. The process of claim 3, wherein the crude reaction product is mixed with ice or ice water, the mixture is strongly agitated and the solid is separated from the liquid by filtration or centrifugation.

5. The process of claim 3, wherein the crude reaction mass is ground and milled with ethanol which causes the selective dissolution of the untransformed urea, then the purified solid is separated from the ethanol by filtration and draining.

6. The process of claim 1, wherein the acid is $H_2SO_4$, HCl, or $H_3PO_4$, and comprises 0.5 to 2.5% by weight of the reaction mixture.

7. The process of claim 1, wherein the mixture is heated progressively to 110° C., and this temperature is maintained for several hours under ordinary or reduced pressure.

8. The process of claim 1 or 7, operated in a continuous manner in a tunnel-oven, the reaction mass being spread as a continuous layer over the surface of a continuous moving belt.

9. A process as in claim 1, wherein the lactosylurea is further treated with formaldehyde in aqueous alkaline medium to convert it to N-methylol-lactosylurea.

* * * * *

UNITED STATES PATENT AND TRADEMARK OFFICE
CERTIFICATE OF CORRECTION

PATENT NO. : 4,267,314
DATED : May 12, 1981
INVENTOR(S) : Jean-Pierre Sachetto et al It is certified that error appears in the above-identified patent and that said Letters Patent are hereby corrected as shown below:

Column 1, line 11, "capable" should read -- able --.

Column 3, lines 5 and 6, "deomposition" should read -- decomposition --.

Column 4, line 67, "poweder" should read -- powder --.

Column 5, line 29, "recylced" should read -- recycled --.

Column 6, line 46, "methode" should read -- method --.

Column 7, line 36, after "250" insert -- 1 --; line 58, "meansurements" should read -- measurements --; line 65 "be" should read -- by --.

Claim 1, line 2, "reminants" should read -- ruminants --.

Signed and Sealed this

Twenty-sixth Day of January 1982

[SEAL]

Attest:

GERALD J. MOSSINGHOFF

Attesting Officer

Commissioner of Patents and Trademarks